United States Patent
Parks

(10) Patent No.: US 11,554,155 B2
(45) Date of Patent: *Jan. 17, 2023

(54) COMPOSITIONS AND METHODS FOR IMPROVING GASTROINTESTINAL FUNCTION

(71) Applicant: Advanced Health Solutions LLC, Gig Harbor, WA (US)

(72) Inventor: Jill Parks, Gig Harbor, WA (US)

(73) Assignee: Advanced Health Solutions LLC, Gig Harbor, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/747,108

(22) Filed: Jan. 20, 2020

(65) Prior Publication Data

US 2021/0220426 A1 Jul. 22, 2021

(51) Int. Cl.
*A61K 36/9068* (2006.01)
*A61K 47/02* (2006.01)
*A61K 47/10* (2017.01)
*A61K 31/12* (2006.01)
*A61K 9/00* (2006.01)
*A61K 47/12* (2006.01)

(52) U.S. Cl.
CPC ........ *A61K 36/9068* (2013.01); *A61K 9/0019* (2013.01); *A61K 9/0053* (2013.01); *A61K 31/12* (2013.01); *A61K 47/02* (2013.01); *A61K 47/10* (2013.01); *A61K 47/12* (2013.01)

(58) Field of Classification Search
CPC .. A61K 36/9068; A61K 47/10; A61K 9/0053; A61K 47/12; A61K 9/0019; A61K 31/12; A61K 47/02; A61K 9/0095; A61K 47/22; A61P 1/00

See application file for complete search history.

(56) References Cited

U.S. PATENT DOCUMENTS

| | | | |
|---|---|---|---|
| 2009/0238905 A1* | 9/2009 | Gurney | A61K 31/045 424/756 |
| 2012/0053239 A1 | 3/2012 | Ehrenpreis | |
| 2012/0219642 A1 | 8/2012 | Nizam | |
| 2013/0344010 A1* | 12/2013 | Pompejus | A61P 1/02 424/50 |
| 2018/0104225 A1 | 4/2018 | Kang et al. | |
| 2018/0116976 A1* | 5/2018 | Westphal | A23L 2/00 |

FOREIGN PATENT DOCUMENTS

| | | |
|---|---|---|
| EP | 3184115 A1 | 6/2017 |
| WO | 2021150638 A1 | 7/2021 |

OTHER PUBLICATIONS

Hawes et al., "A consensus document on bowel preparation before colonoscopy: Prepared by a Task Force From The American Society for Gastrointestinal Endoscopy (ASGE), and the Society of American Gastrointestinal and Endoscopic Surgeons (SAGES)"; Gastrointestinal Endoscopy, vol. 63, Issue 7 (Jun. 2006), p. 894-909.

International Search Report and Written Opinion Received from PCT Application No. PCT/US21/14231, dated Apr. 26, 2021, 7 Pages.

* cited by examiner

*Primary Examiner* — Robert A Wax
*Assistant Examiner* — Quanglong N Truong
(74) *Attorney, Agent, or Firm* — Terrence J. Edwards; TechLaw Ventures, PLLC

(57) ABSTRACT

Compositions and methods for improving gastrointestinal function and reducing the presence of gas bubbles in a gastrointestinal tract. A composition includes an effective amount of ginger root extract for reducing gas bubbles in a gastrointestinal tract and further includes propylene glycol and sodium chloride.

22 Claims, 3 Drawing Sheets

Administering A Composition To A User For Reducing The Presence Of Gas In A Gastrointestinal Tract Of The User.
402

Wherein The Composition Comprises An Effective Amount Of Ginger Root Extract For Reducing The Presence Of The Gas In The Gastrointestinal Tract Of The User.
404

Wherein The Composition Comprises Propylene Glycol.
406

500

```
┌─────────────────────────────────────────────────────────────────────┐
│ Administering A Composition To A User For Reducing The Presence Of Gas In A │
│                  Gastrointestinal Tract Of The User.                │
│                              502                                    │
└─────────────────────────────────────────────────────────────────────┘
                                   │
                                   ▼
┌─────────────────────────────────────────────────────────────────────┐
│ Wherein The Composition Comprises An Effective Amount Of Ginger Root Extract For │
│    Reducing The Presence Of The Gas In The Gastrointestinal Tract Of The User.  │
│                              504                                    │
└─────────────────────────────────────────────────────────────────────┘
                                   │
                                   ▼
┌─────────────────────────────────────────────────────────────────────┐
│       Wherein The Composition Comprises Propylene Glycol And Sodium Chloride.   │
│                              506                                    │
└─────────────────────────────────────────────────────────────────────┘
```

FIG. 5

COMPOSITIONS AND METHODS FOR IMPROVING GASTROINTESTINAL FUNCTION

TECHNICAL FIELD

The disclosure relates generally to compositions of matter and particularly relates to compositions for improving function of the gastrointestinal tract.

BACKGROUND

The digestive system includes the gastrointestinal tract and other accessory organs of digestion. Digestion involves the breakdown of food into smaller components until nutrients can be absorbed and assimilated into the body. The gastrointestinal tract is an organ system within many animals that takes in food, digests the food to extract and absorb energy and nutrients, and expels the remaining waste. The mouth, esophagus, stomach, and intestines are part of the gastrointestinal tract.

The digestive system includes complicated organs performing complex chemical and biological processes. Because the digestive system is very complex, many individuals suffer ailments of the digestive system that may be chronic or transitory. Common ailments of the digestive system include, for example, gastroesophageal reflux disease, irritable bowel syndrome, gallstones, constipation, stomach pains, excessive gas, and others. Some individuals struggle with chronic discomfort or pain associated with digestive system and can therefore benefit from regular administration of composition for improving gastrointestinal health. Further, some individuals experience transitory digestive discomfort and can benefit from natural or medicinal remedies for improving gastrointestinal health or reducing the presence of gas in the gastrointestinal tract.

In light of the foregoing, disclosed herein are compositions and methods for improving function of the gastrointestinal tract and reducing the presence of gas in the gastrointestinal tract.

BRIEF DESCRIPTION OF THE DRAWINGS

Non-limiting and non-exhaustive implementations of the present disclosure are described with reference to the following figures, wherein like reference numerals refer to like parts throughout the various views unless otherwise specified. Advantages of the present disclosure will become better understood with regard to the following description and accompanying drawings where:

FIG. 5 is a schematic flow chart diagram of a method for reducing or eliminating gas in a gastrointestinal tract.

DETAILED DESCRIPTION

Figure 1:
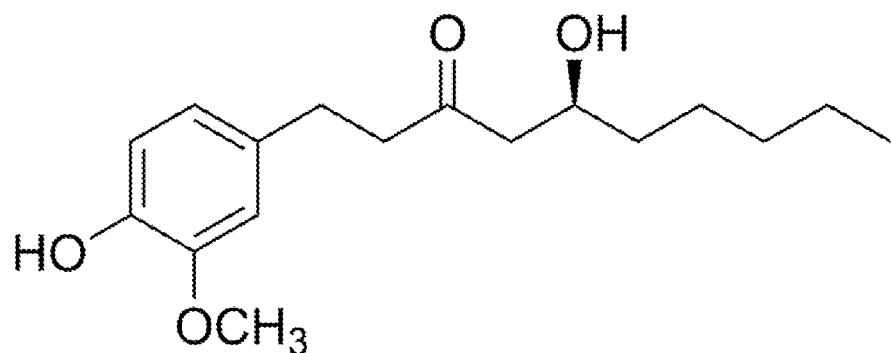
FIG. 1 illustrates the chemical formula of 6-gingerol.

Issues associated with the digestive system and the gastrointestinal (GI) tract are commonly treated with synthetic drugs. Synthetic drugs are expensive and cause genetic and metabolic alterations that can be unsafe for some individuals. Therefore, there is a desire to treat gastrointestinal issues with compositions including natural ingredients and medicinal plants.

The digestive system is an important component of the body. The digestive system includes the gastrointestinal tract whereby food is digested by the body. The gastrointestinal tract begins with the mouth and includes the esophagus, stomach, small intestine, large intestine, rectum, and anus. The human gastrointestinal tract is a single tube which is approximately nine meters long in relaxed condition. A disorder in any portion of the gastrointestinal tract can result in various malfunctions such as diseases of the digestive system and cancer.

Embodiments of the disclosure include compositions and methods for improving gastrointestinal function and reducing symptoms of gas in the gastrointestinal tract. The compositions and methods disclosed herein are water soluble to increase absorption of the active ingredients and improve the efficacy of the active ingredients. In an embodiment, a composition includes ginger root extract and specifically includes 6-gingerol and 6-shogaol. The composition includes an effective amount of ginger root extract for reducing gas in the gastrointestinal tract and improving gastrointestinal function.

Ginger (*Zingiber officinale*) is a member of the Zingiberaceae family. Chemical analysis of ginger shows that it includes over 400 different compounds. The major components in ginger rhizomes are carbohydrates (50-70%), lipids (3-8%), terpenes, and phenolic compounds. Terpene components of ginger include zingiberene, β-bisabolene, α-farnesene, β-sesquiphellandrene, and α-curcumene. Phenolic compounds include gingerol, paradols, and shogaol. Gingerol and shogaol are found in higher quantities than other components of ginger. Ginger further includes amino acids, raw fiber, ash, protein, phytosterols, vitamins, and minerals.

The aromatic constituents of ginger include zingiberene and bisabolene. The pungent constituents include the gingerol-related compounds and the shogaol-related compounds. The gingerol- and shogaol-related compounds within ginger rhizome include 6-paradol, 1-dehydrogingerdione, and 6-diarylhgeptanoids.

Ginger and its components have been shown to modulate a wide range of signaling molecules. Ginger may upregulate or downregulate the gene expression of multiple different genes depending on the target and cellular context. Ginger extract increases production of antioxidant enzymes including reduced glutathione (GSH), superoxide dismutase (SOD), and glutathione peroxidase. Ginger additionally targets phase II detoxification enzymes as well as nuclear localization of the Nrf2 pathway.

Additionally, a number of targets of ginger and its components have been documented in different cancer prevention models, including transcription factors, enzymes, inflammatory mediators, protein kinases, drug resistance proteins, adhesion molecules, growth factor receptors, cell-cycle regulatory proteins, cell-survival proteins, chemokines, and chemokine receptors. In different gastrointestinal cancers, ginger extract inhibits transcription factor NF-kB, inflammatory cytokine, TNF-α, and other enzymes and proteins, which include xanthine oxidase and myeloperoxidase.

The active ingredients of ginger, including 6-gingerol and 6-shogaol, target several cellular molecules that contribute to cell survival, cell proliferation, and angiogenesis. 6-gingerol modulates NF-κB, STAT3, Rb, MAPK, PI3K, Akt, ERK, cIAP1, cyclin A, Cdk, cathepsin D, and caspase-3/7.

Similarly, 6-shogaol targets NF-κB, STAT3, MAPK, PI3k/Akt $Ca^{2+}$ signals, COX-2, cyclin D1, survivin, cIAP-1, XIAP, Bcl-2, MMP-9, caspase activation, ER stress, and eIF2α. Besides these, ginger component zerumbone modulates NF-κB, p53 VEGF, p21, and CXCR4 expression.

In the following description of the disclosure, reference is made to the accompanying drawings, which form a part hereof, and in which is shown by way of illustration specific implementations in which the disclosure may be practiced. It is understood that other implementations may be utilized, and structural changes may be made without departing from the scope of the disclosure.

Before the structures, systems, methods, and compositions for improving gastrointestinal function are disclosed and described, it is to be understood that this disclosure is not limited to the particular structures, configurations, process steps, and materials disclosed herein as such structures, configurations, process steps, and materials may vary somewhat. It is also to be understood that the terminology employed herein is used for the purpose of describing particular embodiments only and is not intended to be limiting since the scope of the disclosure will be limited only by the appended claims and equivalents thereof.

In describing and claiming the subject matter of the disclosure, the following terminology will be used in accordance with the definitions set out below.

As used herein, the terms "comprising," "including," "containing," "characterized by," and grammatical equivalents thereof are inclusive or open-ended terms that do not exclude additional, unrecited elements or method steps.

As used herein, the phrase "consisting of" and grammatical equivalents thereof exclude any element, step, or ingredient not specified in the claim.

As used herein, the phrase "consisting essentially of" and grammatical equivalents thereof limit the scope of a claim to the specified ingredients, materials or steps and those that do not materially affect the basic and novel characteristic or characteristics of the claimed disclosure.

As used herein, "effective amount" means an amount of an ingredient or a component of the product that is nontoxic, but sufficient to provide the desired effect and performance at a reasonable benefit/risk ratio attending any dietary supplement or product. For example, an effective amount of a vitamin or mineral is an amount sufficient to prevent a deficiency thereof and to reduce the incidence of some adverse effects.

Unless defined otherwise, all technical and scientific terms used herein have the same meanings as commonly understood by one of ordinary skill in the art to which this disclosure pertains and belongs.

Reference will now be made in detail to the exemplary embodiments, examples of which are illustrated in the accompanying drawings. Wherever possible, the same reference numbers are used throughout the drawings to refer to the same or like parts. It is further noted that elements disclosed with respect to particular embodiments are not restricted to only those embodiments in which they are described. For example, an element described in reference to one embodiment or figure, may be alternatively included in another embodiment or figure regardless of whether or not those elements are shown or described in another embodiment or figure. In other words, elements in the figures may be interchangeable between various embodiments disclosed herein, whether shown or not.

Referring now to the figures, FIG. 1 illustrates the chemical formula of 6-gingerol, which is a form of gingerol. Gingerols are chemical compounds found in ginger root extract. Gingerols exhibit antioxidant, anti-tumor, and anti-inflammatory properties. Ginger root ex extract is shown to be effective at reducing or eliminating the presence of gas bubbles in the gastrointestinal tract.

Gingerols exhibit powerful medicinal properties. Specifically, gingerols reduce symptoms of nausea, including nausea associated with pregnancy or sea sickness. Gingerols may relieve nausea or vomiting induced by drugs such as general anesthesia or chemotherapy. Gingerols are effective against exercise-induced muscle pain and soreness and may reduce the time to recover from exercise-induced pain or injury. Additionally, gingerols exhibit anti-inflammatory effects and can reduce bone degeneration associated with osteoarthritis. Gingerols are associated with lower blood sugars and improving heart disease risk factors. Further, gingerols and other components of ginger root extract are shown to relieve symptoms of chronic indigestion and other ailments associated with the digestive system.

In an embodiment, a composition includes ginger root extract. The ginger root extract may include, for example, 6-gingerol and 6-shogaol. In an embodiment, the ginger root extract is dried ginger root 1:4 extract in 70% organic cane alcohol. In an embodiment, the ginger root extract is dried ginger root 1:4 extract in 60% organic cane alcohol. In an embodiment, the ginger root extract is dried ginger root 1:4 extract in 80% organic cane alcohol.

Figure 2:
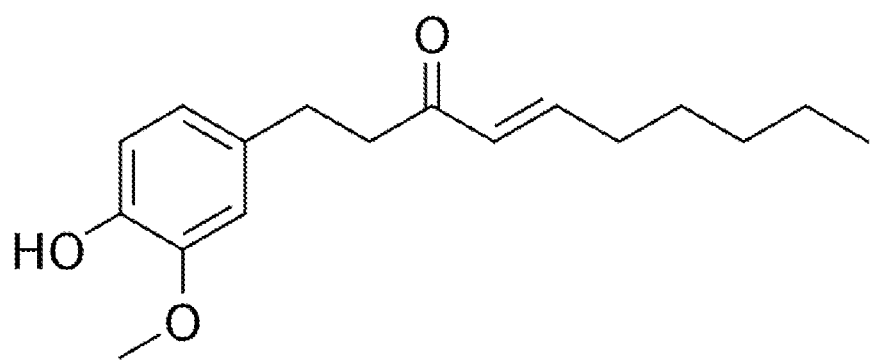
FIG. 2 illustrates the chemical formula of 6-shogaol.

FIG. 2 illustrates the chemical formula of 6-shogaol, which is a form of shogaol. Shogaols are pungent constituents of ginger root extract similar in chemical structure to gingerols as shown in FIG. 1. Shogaols as a group include 4-shogaol, 6-shogaol, 10-shogaol, and 12-shogaol, which are all found in ginger. Shogaols are artifacts formed during storage or through excess heat and may be created by a dehydration reaction of gingerols.

Figure 3:
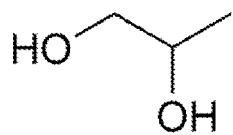
FIG. 3 illustrates the chemical formula of propylene glycol.

FIG. 3 illustrates the chemical formula of propylene glycol. The International Union of Pure and Applied Chemistry (IUPAC) name for propylene glycol is propane-1,2-diol. Propylene glycol is an organic compound with the chemical formula $CH_3CH(OH)CH_2OH$. Propylene glycol is a viscous, colorless liquid that includes two alcohol groups. Propylene glycol is miscible with a range of solvents, including water, acetone, and chloroform. In general, propylene glycol is non-irritation, has a low volatility, and a very low toxicity. Propylene glycol is chiral is sometimes referred to as α-propylene glycol to distinguish from the isomer propane-1,3-diol, known as β-propylene glycol.

The oral toxicity of propylene glycol is very low, and large quantities are required to cause perceptible health effects in humans. Propylene glycol is metabolized in the human body into pyruvic acid as a normal part of the glucose-metabolism process, acetic acid, lactic acid, and propionaldehyde. The potential for long-term oral toxicity of propylene glycol is low and the substance is therefore recognized as safe. Propylene glycol is essentially non-irritating to human skin and other human tissues.

Propylene glycol absorbs water and can be used a solvent. Because propylene glycol is water soluble, propylene glycol can be used in conjunction with ginger root extract and a salt to significantly improve gastrointestinal function, reduce symptoms of gas in the gastrointestinal tract, and improve overall health of the gastrointestinal system. In an embodiment, a composition includes propylene glycol, ginger root extract, and a salt. The composition is provided to user for oral administration. The composition is effective for reducing or eliminating gas bubbles that are naturally present in the gastrointestinal tract, and therefore, the composition is effective for reducing uncomfortable symptoms of gas in the gastrointestinal tract. The composition is especially effective because the combination of propylene glycol and a salt increases absorption of the ginger root extract by a body. This is a significant improvement over traditional ginger supplements known in the art.

Figure 4:
FIG. 4 is a schematic flow chart diagram of a method for reducing or eliminating gas bubbles in a gastrointestinal tract.
Figure 4:
Figure 4:

FIG. 4 is a schematic diagram of a method 400 for reducing the presence of gas bubbles in a gastrointestinal tract of a user. The method 400 begins and a medical practitioner or computer program administers at 402 a composition to a user, wherein the composition is effective for reducing the presence of gas bubbles in a gastrointestinal tract of the user. The method 400 is such that the composition includes an effective amount of ginger root extract for reducing the presence of the gas bubbles in the gastrointestinal tract of the user (see 404). The method 400 is such that the composition includes propylene glycol (see 406).

FIG. 5 is a schematic diagram of a method 500 for reducing the presence of gas bubbles in a gastrointestinal tract of a user. The method 500 begins and a medical practitioner or computer program administers at 502 a composition to a user, wherein the composition is effective for reducing the presence of gas bubbles in a gastrointestinal tract of the user. The method 500 is such that the composition includes an effective amount of ginger root extract for reducing the presence of the gas bubbles in the gastrointestinal tract of the user (see 504). The method 500 is such that the composition includes propylene glycol and sodium chloride (see 506).

Examples

The following examples pertain to further embodiments.
Table 1 below shows an example embodiment of the composition.

TABLE 1

| Component | Weight Percent Total Composition |
| --- | --- |
| Water | 59.6 |
| Propylene glycol | 20.3 |
| Ginger root extract | 11.2 |
| Citric acid | 4.6 |
| Ascorbic acid | 3.0 |
| Sodium chloride | 1.2 |
| Potassium sorbate | 0.1 |

Table 2 below shows an example embodiment of the composition.

TABLE 2

| Component | Weight Percent Total Composition |
| --- | --- |
| Water | 65.2 |
| Propylene glycol | 16.8 |
| Ginger root extract | 8.4 |
| Citric acid | 4.2 |
| Ascorbic acid | 4.2 |
| Sodium chloride | 1.1 |
| Potassium sorbate | 0.1 |

Table 3 below shows an example embodiment of the composition.

TABLE 3

| Component | Weight Percent Total Composition |
| --- | --- |
| Water | 55.7 |
| Propylene glycol | 19.4 |

TABLE 3-continued

| Component | Weight Percent Total Composition |
| --- | --- |
| Ginger root extract | 15.7 |
| Citric acid | 3.2 |
| Ascorbic acid | 4.1 |
| Sodium chloride | 1.5 |
| Potassium sorbate | 0.4 |

Table 4 below shows an example embodiment of the composition.

TABLE 4

| Component | Weight Percent Total Composition |
| --- | --- |
| Water | 47.6 |
| Propylene glycol | 23.4 |
| Ginger root extract | 10.9 |
| Citric acid | 7.1 |
| Ascorbic acid | 8.5 |
| Sodium chloride | 2.5 |

Table 5 below shows an example embodiment of the composition.

TABLE 5

| Component | Weight Percent Total Composition |
| --- | --- |
| Water | 30.4 |
| Propylene glycol | 33.0 |
| Ginger root extract | 25.0 |
| Citric acid | 5.2 |
| Ascorbic acid | 4.8 |
| Sodium chloride | 1.6 |

Table 6 below shows an example embodiment of the composition.

TABLE 6

| Component | Weight Percent Total Composition |
| --- | --- |
| Water | 22.9 |
| Propylene glycol | 32.5 |
| Ginger root extract | 10.4 |
| Citric acid | 10.5 |
| Ascorbic acid | 9.1 |
| Sodium chloride | 14.6 |

According to one or more embodiments of the disclosure, a composition may include a combination of all of the following ingredients, or some, but not all, of the following ingredients:
 a) Propylene glycol;
 b) Ginger root extract;
 c) 6-gingerol;
 d) 6-shogaol;
 e) Peppermint extract;
 f) Citric acid;
 g) Ascorbic acid;
 h) Sodium chloride;
 i) Potassium sorbate; and/or
 j) Water.

Embodiments of the composition may comprise, for example, concentrations of propylene glycol as follows:
 a1) from about 10 wt % to about 35 wt % the total composition;
 a2) from about 10 wt % to about 45 wt % the total composition;

a3) from about 10 wt % to about 30 wt % the total composition;
a4) from about 10 wt % to about 25 wt % the total composition;
a5) from about 10 wt % to about 20 wt % the total composition;
a6) from about 10 wt % to about 15 wt % the total composition;
a7) from about 15 wt % to about 45 wt % the total composition;
a8) from about 20 wt % to about 45 wt % the total composition;
a9) from about 25 wt % to about 45 wt % the total composition;
a10) from about 30 wt % to about 45 wt % the total composition;
a11) from about 35 wt % to about 45 wt % the total composition;
a12) from about 40 wt % to about 45 wt % the total composition;
a13) from about 40 wt % to about 80 wt % the total composition;
a14) from about 30 wt % to about 90 wt % the total composition;
a15) from about 20 wt % to about 90 wt % the total composition;
a16) from about 45 wt % to about 80 wt % the total composition;
a17) from about 50 wt % to about 80 wt % the total composition;
a18) from about 60 wt % to about 80 wt % the total composition;
a19) from about 60 wt % to about 75 wt % the total composition;
a20) from about 60 wt % to about 70 wt % the total composition;
a21) from about 60 wt % to about 65 wt % the total composition;
a22) from about 50 wt % to about 70 wt % the total composition;
a23) from about 52 wt % to about 70 wt % the total composition;
a24) from about 54 wt % to about 70 wt % the total composition;
a25) from about 56 wt % to about 70 wt % the total composition;
a26) from about 58 wt % to about 70 wt % the total composition;
a27) from about 60 wt % to about 70 wt % the total composition;
a28) from about 62 wt % to about 70 wt % the total composition;
a29) from about 64 wt % to about 70 wt % the total composition;
a30) from about 66 wt % to about 70 wt % the total composition;
a31) from about 62 wt % to about 67 wt % the total composition;
a32) from about 63 wt % to about 67 wt % the total composition;
a33) from about 64 wt % to about 67 wt % the total composition; or
a34) from about 64 wt % to about 66 wt % the total composition.
Embodiments of the composition may comprise, for example, concentrations of ginger root extract as follows:
b1) from about 3 wt % to about 15 wt % the total composition;
b2) from about 3 wt % to about 14 wt % the total composition;
b3) from about 3 wt % to about 13 wt % the total composition;
b4) from about 3 wt % to about 12 wt % the total composition;
b5) from about 3 wt % to about 11 wt % the total composition;
b6) from about 3 wt % to about 10 wt % the total composition;
b7) from about 3 wt % to about 9 wt % the total composition;
b8) from about 4 wt % to about 15 wt % the total composition;
b9) from about 5 wt % to about 15 wt % the total composition;
b10) from about 6 wt % to about 15 wt % the total composition;
b11) from about 7 wt % to about 15 wt % the total composition;
b12) from about 8 wt % to about 15 wt % the total composition;
b13) from about 7 wt % to about 9 wt % the total composition;
b14) from about 6 wt % to about 10 wt % the total composition;
b15) from about 6 wt % to about 9 wt % the total composition;
b16) from about 5 wt % to about 12 wt % the total composition;
b17) from about 5 wt % to about 10 wt % the total composition;
b18) from about 2 wt % to about 20 wt % the total composition;
b19) from about 2 wt % to about 25 wt % the total composition;
b20) from about 2 wt % to about 30 wt % the total composition;
b21) from about 2 wt % to about 35 wt % the total composition;
b22) from about 2 wt % to about 40 wt % the total composition;
b23) from about 5 wt % to about 40 wt % the total composition;
b24) from about 5 wt % to about 45 wt % the total composition; or
b25) from about 5 wt % to about 50 wt % the total composition.
Embodiments of the composition may comprise, for example, concentrations of peppermint extract as follows:
e1) from about 3 wt % to about 15 wt % the total composition;
e2) from about 3 wt % to about 14 wt % the total composition;
e3) from about 3 wt % to about 13 wt % the total composition;
e4) from about 3 wt % to about 12 wt % the total composition;
e5) from about 3 wt % to about 11 wt % the total composition;
e6) from about 3 wt % to about 10 wt % the total composition;
e7) from about 3 wt % to about 9 wt % the total composition;

e8) from about 4 wt % to about 15 wt % the total composition;
e9) from about 5 wt % to about 15 wt % the total composition;
e10) from about 6 wt % to about 15 wt % the total composition;
e11) from about 7 wt % to about 15 wt % the total composition;
e12) from about 8 wt % to about 15 wt % the total composition;
e13) from about 7 wt % to about 9 wt % the total composition;
e14) from about 6 wt % to about 10 wt % the total composition;
e15) from about 6 wt % to about 9 wt % the total composition;
e16) from about 5 wt % to about 12 wt % the total composition;
e17) from about 5 wt % to about 10 wt % the total composition;
e18) from about 2 wt % to about 20 wt % the total composition;
e19) from about 2 wt % to about 25 wt % the total composition;
e20) from about 2 wt % to about 30 wt % the total composition;
e21) from about 2 wt % to about 35 wt % the total composition;
e22) from about 2 wt % to about 40 wt % the total composition;
e23) from about 5 wt % to about 40 wt % the total composition;
e24) from about 5 wt % to about 45 wt % the total composition; or
e25) from about 5 wt % to about 50 wt % the total composition.

Embodiments of the composition may comprise, for example, concentrations of citric acid as follows:
f1) from about 2 wt % to about 20 wt % the total composition;
f2) from about 2 wt % to about 19 wt % the total composition;
f3) from about 2 wt % to about 18 wt % the total composition;
f4) from about 2 wt % to about 17 wt % the total composition;
f5) from about 2 wt % to about 16 wt % the total composition;
f6) from about 2 wt % to about 15 wt % the total composition;
f7) from about 1 wt % to about 10 wt % the total composition;
f8) from about 2 wt % to about 10 wt % the total composition;
f9) from about 3 wt % to about 10 wt % the total composition;
f10) from about 4 wt % to about 10 wt % the total composition;
f11) from about 5 wt % to about 10 wt % the total composition;
f12) from about 1 wt % to about 9 wt % the total composition;
f13) from about 1 wt % to about 8 wt % the total composition;
f14) from about 1 wt % to about 7 wt % the total composition;
f15) from about 1 wt % to about 6 wt % the total composition;
f16) from about 2 wt % to about 5 wt % the total composition;
f17) from about 3 wt % to about 5 wt % the total composition;
f18) from about 1 wt % to about 15 wt % the total composition;
f19) from about 1 wt % to about 20 wt % the total composition;
f20) from about 1 wt % to about 25 wt % the total composition;
f21) from about 1 wt % to about 30 wt % the total composition; or
f22) from about 1 wt % to about 35 wt % the total composition.

Embodiments of the composition may comprise, for example, concentrations of ascorbic acid as follows:
g1) from about 2 wt % to about 20 wt % the total composition;
g2) from about 2 wt % to about 19 wt % the total composition;
g3) from about 2 wt % to about 18 wt % the total composition;
g4) from about 2 wt % to about 17 wt % the total composition;
g5) from about 2 wt % to about 16 wt % the total composition;
g6) from about 2 wt % to about 15 wt % the total composition;
g7) from about 1 wt % to about 10 wt % the total composition;
g8) from about 2 wt % to about 10 wt % the total composition;
g9) from about 3 wt % to about 10 wt % the total composition;
g10) from about 4 wt % to about 10 wt % the total composition;
g11) from about 5 wt % to about 10 wt % the total composition;
g12) from about 1 wt % to about 9 wt % the total composition;
g13) from about 1 wt % to about 8 wt % the total composition;
g14) from about 1 wt % to about 7 wt % the total composition;
g15) from about 1 wt % to about 6 wt % the total composition;
g16) from about 2 wt % to about 5 wt % the total composition;
g17) from about 3 wt % to about 5 wt % the total composition;
g18) from about 1 wt % to about 15 wt % the total composition;
g19) from about 1 wt % to about 20 wt % the total composition;
g20) from about 1 wt % to about 25 wt % the total composition;
g21) from about 1 wt % to about 30 wt % the total composition; or
g22) from about 1 wt % to about 35 wt % the total composition.

Embodiments of the disclosure may comprise, for example, concentrations of sodium chloride as follows:
h1) from about 1 wt % to about 30 wt % the total composition;

h2) from about 1 wt % to about 40 wt % the total composition;
h3) from about 1 wt % to about 25 wt % the total composition;
h4) from about 1 wt % to about 23 wt % the total composition;
h5) from about 1 wt % to about 20 wt % the total composition;
h6) from about 1 wt % to about 18 wt % the total composition;
h7) from about 1 wt % to about 15 wt % the total composition;
h8) from about 1 wt % to about 13 wt % the total composition;
h9) from about 1 wt % to about 10 wt % the total composition;
h10) from about 1 wt % to about 8 wt % the total composition;
h11) from about 1 wt % to about 5 wt % the total composition;
h12) from about 1 wt % to about 3 wt % the total composition;
h13) from about 1 wt % to about 2 wt % the total composition;
h14) from about 3 wt % to about 30 wt % the total composition;
h15) from about 5 wt % to about 30 wt % the total composition;
h16) from about 8 wt % to about 30 wt % the total composition;
h17) from about 10 wt % to about 30 wt % the total composition;
h18) from about 13 wt % to about 30 wt % the total composition;
h19) from about 15 wt % to about 30 wt % the total composition;
h20) from about 18 wt % to about 30 wt % the total composition;
h21) from about 20 wt % to about 30 wt % the total composition;
h22) from about 25 wt % to about 30 wt % the total composition;

The foregoing percentages, concentrations, and ratios are presented by example only and are not intended to be exhaustive or to limit the disclosure to the precise percentages, concentrations, and ratios disclosed. It should be appreciated that each value that falls within a disclosed range is disclosed as if it were individually disclosed as set forth herein. For example, a range indicating a weight percent from about 8% to about 14% additionally includes ranges beginning or ending with all values within that range, including for example a range beginning at 8.1%, 8.2%, 8.3%, 9%, 10%, 11%, 12%, and so forth.

Also, according to one or more non-limiting embodiments of the disclosure, any of the concentrations for ingredients for a combination of the ingredients (a) thru (i), for example, as listed above, may indicate the concentration for other ingredients listed above.

Example 1 is a composition. The composition includes an effective amount of ginger root extract for reducing gas bubbles in a gastrointestinal tract. The composition includes propylene glycol.

Example 2 is a composition as in Example 1, further comprising one or more of citric acid or ascorbic acid.

Example 3 is a composition as in any of Examples 1-2, further comprising one or more of sodium chloride or potassium sorbate.

Example 4 is a composition as in any of Examples 1-3, wherein the effective amount of the ginger root extract comprises from about 4 wt % to about 25 wt % the composition.

Example 5 is a composition as in any of Examples 1-4, wherein the propylene glycol comprises from about 10 wt % to about 30 wt % the composition.

Example 6 is a composition as in any of Examples 1-5, further comprising water, wherein the water comprises from about 50 wt % to about 85 wt % the composition.

Example 7 is a composition as in any of Examples 1-6, wherein the composition is prepared for oral administration.

Example 8 is a composition as in any of Examples 1-7, wherein the composition is prepared for intravenous or intramuscular administration.

Example 9 is a composition as in any of Examples 1-8, wherein the effective amount of the ginger root extract comprises 6-gingerol and 6-shogaol.

Example 10 is a composition as in any of Examples 1-9, wherein the composition is water soluble.

Example 11 is a method. The method includes providing a composition to a user for reducing gas bubbles in a gastrointestinal tract of the user. The composition includes an effective amount of ginger root extract for reducing the gas bubbles in the gastrointestinal tract of the user. The composition includes propylene glycol.

Example 12 is a method as in Example 11, wherein the composition further comprises one or more of citric acid or ascorbic acid.

Example 13 is a method as in any of Examples 11-12, wherein the composition further comprises one or more of sodium chloride or potassium sorbate.

Example 14 is a method as in any of Examples 11-13, wherein the effective amount of the ginger root extract comprises from about 4 wt % to about 25 wt % the composition.

Example 15 is a method as in any of Examples 11-14, wherein the propylene glycol comprises from about 10 wt % to about 30 wt % the composition.

Example 16 is a method as in any of Examples 11-15, wherein the composition further comprises water, and wherein the water comprises from about 50 wt % to about 85 wt % the composition.

Example 17 is a method as in any of Examples 11-16, wherein the composition is prepared for oral administration.

Example 18 is a method as in any of Examples 11-17, wherein the composition is prepared for intravenous or intramuscular administration.

Example 19 is a method as in any of Examples 11-18, wherein the effective amount of the ginger root extract comprises 6-gingerol and 6-shogaol.

Example 20 is a method as in any of Examples 11-19, wherein the composition is water soluble.

The foregoing description has been presented for purposes of illustration. It is not exhaustive and does not limit the invention to the precise forms or embodiments disclosed. Modifications and adaptations will be apparent to those skilled in the art from consideration of the specification and practice of the disclosed embodiments. For example, components described herein may be removed and other components added without departing from the scope or spirit of the embodiments disclosed herein or the appended claims.

Other embodiments will be apparent to those skilled in the art from consideration of the specification and practice of the disclosure disclosed herein. It is intended that the specification and examples be considered as exemplary only, with a true scope and spirit of the invention being indicated by the following claims.

What is claimed is:

1. A composition comprising:
   an effective amount of ginger root extract for reducing gas in a gastrointestinal tract of a user;
   an effective amount of propylene glycol for increasing absorption of the effective amount of the ginger root extract by the user; and
   an effective amount of sodium chloride for increasing absorption of the effective amount of the ginger root extract by the user in combination with the effective amount of the propylene glycol.

2. The composition of claim 1, further comprising of citric acid, ascorbic acid, and potassium sorbate, wherein the composition comprises equal amounts of the citric acid and the ascorbic acid.

3. The composition of claim 1, wherein the effective amount of the propylene glycol is further effective for making the composition water soluble.

4. The composition of claim 1, wherein the effective amount of the ginger root extract comprises from about 3 wt. % to about 25 wt. % the composition.

5. The composition of claim 1, wherein the effective amount of the propylene glycol comprises from about 10 wt. % to about 40 wt. % the composition.

6. The composition of claim 1, further comprising water, wherein the water comprises from about 20 wt. % to about 85 wt. % the composition.

7. The composition of claim 1, wherein the composition is prepared for oral administration and is water soluble.

8. The composition of claim 1, wherein the composition is prepared for intravenous or intramuscular administration.

9. The composition of claim 1, wherein the effective amount of the ginger root extract comprises 6-gingerol and 6-shogaol.

10. The composition of claim 1, wherein the composition is water soluble and wherein:
    the effective amount of the ginger root extract comprises from about 10 wt. % to about 20 wt. % the composition;
    the effective amount of the propylene glycol comprises from about 10 wt. % to about 20 wt. % the composition; and
    the effective amount of the sodium chloride comprises from about 1 wt. % to about 5 wt. % the composition.

11. A method comprising:
    providing a composition to a user for reducing gas in a gastrointestinal tract of the user, wherein the composition comprises:
      an effective amount of ginger root extract for reducing the gas in the gastrointestinal tract of the user;
      an effective amount of propylene glycol for increasing absorption of the effective amount of the ginger root extract by the user; and
      an effective amount of sodium chloride for increasing absorption of the effective amount of the ginger root extract by the user in combination with the effective amount of the propylene glycol.

12. The method of claim 11, wherein the composition further comprises one or more of citric acid, ascorbic acid, and potassium sorbate, wherein the composition comprises equal amounts of the citric acid and the ascorbic acid.

13. The method of claim 11, wherein the effective amount of the propylene glycol is further effective for making the composition water soluble.

14. The method of claim 11, wherein the effective amount of the ginger root extract comprises from about 3 wt. % to about 25 wt. % the composition.

15. The method of claim 11, wherein the effective amount of the propylene glycol comprises from about 10 wt. % to about 40 wt. % the composition.

16. The method of claim 11, wherein the composition further comprises water, and wherein the water comprises from about 20 wt. % to about 85 wt. % the composition.

17. The method of claim 11, wherein the composition is prepared for oral administration and is water soluble.

18. The method of claim 11, wherein the composition is prepared for intravenous or intramuscular administration.

19. The method of claim 11, wherein the effective amount of the ginger root extract comprises 6-gingerol and 6-shogaol.

20. The method of claim 11, wherein the composition is water soluble and wherein:
    the effective amount of the ginger root extract comprises from about 10 wt. % to about 20 wt. % the composition;
    the effective amount of the propylene glycol comprises from about 10 wt. % to about 20 wt. % the composition; and
    the effective amount of the sodium chloride comprises from about 1 wt. % to about 5 wt. % the composition.

21. The composition of claim 1, wherein the composition further comprises water, citric acid, ascorbic acid, and potassium sorbate, and wherein:
    the effective amount of the ginger root extract comprises from about 10 wt. % to about 35 wt. % the composition;
    the effective amount of the propylene glycol comprises from about 10 wt. % to about 35 wt. % the composition;
    the effective amount of the sodium chloride comprises from about 1 wt. % to about 2 wt. % the composition;
    the water comprises from about 50 wt. % to about 85 wt. % the composition;
    the citric acid comprises from about 2 wt. % to about 7 wt. % the composition;
    the ascorbic acid comprises from about 2 wt. % to about 7 wt. % the composition; and
    the potassium sorbate comprises from about 0.1 wt. % to about 0.4 wt. % the composition.

22. The composition of claim 2, wherein the composition comprises one or more of:
    a 1:1 ratio of the effective amount of the propylene glycol and the effective amount of the ginger root extract by weight; or
    a 1:1 ratio of the citric acid and the ascorbic acid by weight.

* * * * *